(12) United States Patent
Schumacher

(10) Patent No.: US 11,654,260 B1
(45) Date of Patent: May 23, 2023

(54) ULTRASOUND-PLACED PAIN MANAGEMENT SYSTEM AND METHOD WITH SUBCUTANEOUS CATHETER

(71) Applicant: Maho Med Tech, LLC, Carlotte Amalie, VI (US)

(72) Inventor: Shawn D. Schumacher, Corvallis, OR (US)

(73) Assignee: Maho Med Tech, LLC, Charlotte Amalie, VI (US)

( * ) Notice: Subject to any disclaimer, the term of this patent is extended or adjusted under 35 U.S.C. 154(b) by 0 days.

(21) Appl. No.: 17/939,631

(22) Filed: Sep. 7, 2022

Related U.S. Application Data

(63) Continuation-in-part of application No. 17/518,815, filed on Nov. 4, 2021, now abandoned.

(51) Int. Cl.
*A61M 25/00* (2006.01)
*A61M 25/01* (2006.01)
*A61B 8/08* (2006.01)

(52) U.S. Cl.
CPC ....... *A61M 25/0043* (2013.01); *A61B 8/0841* (2013.01); *A61M 25/0108* (2013.01); *A61M 2025/0057* (2013.01)

(58) Field of Classification Search
CPC ............ A61B 8/085; A61B 2017/3413; A61B 2034/2063; A61B 8/0833; A61M 25/0108; A61N 1/0551; A61N 2005/1058
See application file for complete search history.

(56) References Cited

U.S. PATENT DOCUMENTS

| | | | |
|---|---|---|---|
| 4,435,173 A | * | 3/1984 | Siposs ................. A61M 5/1456 D24/111 |
| 4,569,675 A | | 2/1986 | Prosl et al. |
| 4,774,951 A | | 10/1988 | Osypka |
| 4,973,305 A | | 11/1990 | Goltzer |
| 5,167,638 A | | 12/1992 | Felix et al. |
| 5,403,283 A | | 4/1995 | Luther |
| 5,688,237 A | | 11/1997 | Rozga et al. |
| 5,735,829 A | | 4/1998 | Cherian |
| 5,743,873 A | | 4/1998 | Cai et al. |
| 6,120,492 A | | 9/2000 | Finch et al. |
| 6,532,387 B1 | * | 3/2003 | Marchitto ............. A61M 31/00 606/15 |
| 7,174,923 B2 | | 2/2007 | Schorn et al. |
| 7,513,892 B1 | | 4/2009 | Haarala et al. |
| 8,376,960 B2 | * | 2/2013 | Olson ..................... A61L 31/14 604/95.04 |
| 9,610,438 B2 | | 4/2017 | Schilling |
| 2002/0032416 A1 | | 3/2002 | Utterberg et al. |

(Continued)

*Primary Examiner* — Theodore J Stigell
(74) *Attorney, Agent, or Firm* — Law Office of Mark Brown, LLC; Mark E. Brown

(57) ABSTRACT

A catheter system includes a medication dispenser located external to a patient. A subcutaneous port is placed internally to the patient and receives a quantity of medication. The port can be filled from a syringe or medication dispensing system. An echogenic catheter can be placed in proximity to a patient's nerve or nerve center using a point-of-care ultrasound imaging system. A method of administering a nerve block or other medication subcutaneously to a patient includes the steps of placing a subcutaneous port using ultrasound imaging for guidance and administering pharmacologic agents via a catheter connected to the port.

1 Claim, 4 Drawing Sheets

(56) References Cited

U.S. PATENT DOCUMENTS

| | | | |
|---|---|---|---|
| 2002/0087177 A1* | 7/2002 | Wallace | A61B 17/12186 |
| | | | 606/157 |
| 2003/0094731 A1 | 5/2003 | Simpson | |
| 2005/0192638 A1* | 9/2005 | Gelfand | A61N 1/326 |
| | | | 604/890.1 |
| 2005/0240155 A1 | 10/2005 | Conlon | |
| 2007/0008314 A1 | 4/2007 | Simpson | |
| 2008/0058702 A1 | 3/2008 | Arndt et al. | |
| 2009/0149838 A1* | 6/2009 | Cassada | A61M 25/0021 |
| | | | 604/890.1 |
| 2010/0041990 A1 | 2/2010 | Schlitt et al. | |
| 2011/0112511 A1* | 5/2011 | Singer | A61M 19/00 |
| | | | 604/512 |
| 2011/0301570 A1 | 12/2011 | Huet | |
| 2012/0059308 A1* | 3/2012 | Hsu | A61M 19/00 |
| | | | 604/528 |
| 2013/0053783 A1 | 2/2013 | Szweda et al. | |
| 2013/0131501 A1 | 3/2013 | Blaivas et al. | |
| 2015/0080856 A1 | 3/2015 | Stroup et al. | |
| 2019/0069948 A1* | 3/2019 | Herth | A61B 18/1492 |
| 2019/0117883 A1 | 4/2019 | Abrams et al. | |
| 2020/0222630 A1 | 7/2020 | Hemati et al. | |
| 2020/0297307 A1 | 9/2020 | Khalaj et al. | |
| 2022/0133401 A1* | 5/2022 | O'Brien | A61B 18/1482 |
| | | | 606/41 |

* cited by examiner

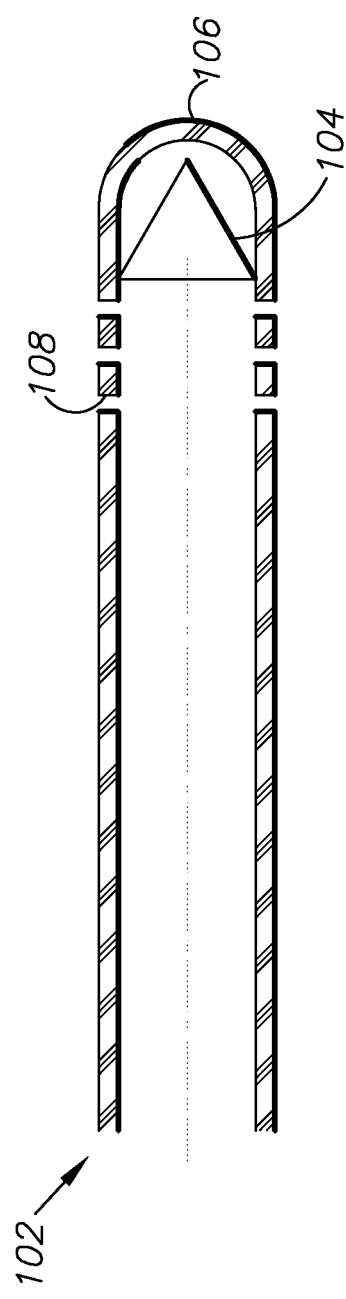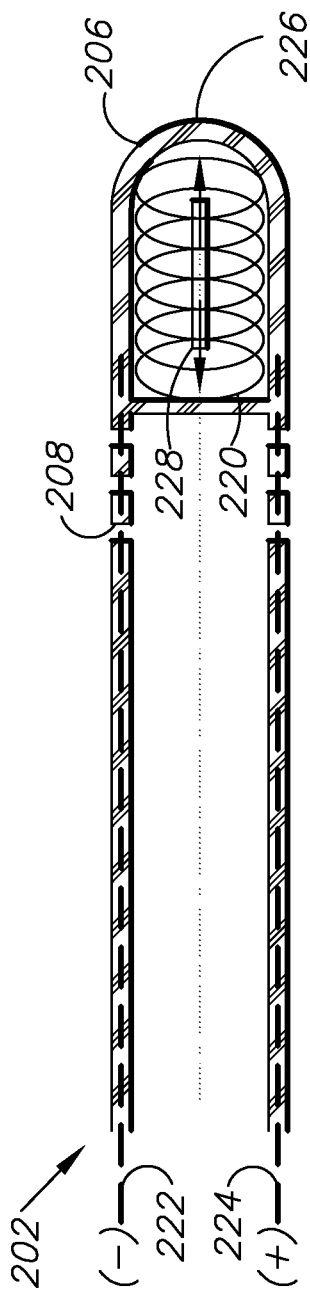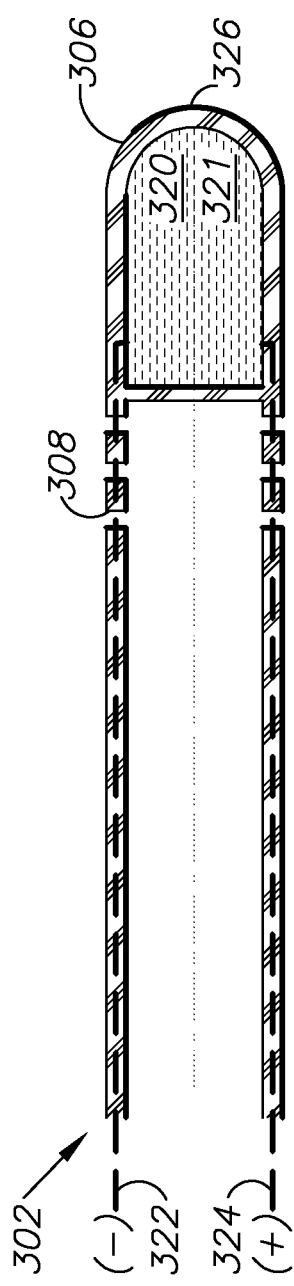
FIG. 3 Echogenic Marker
FIG. 4 Solenoid/Magnet
FIG. 5 MR or ER Fluid Phase Change Agent MEMS/pMUT

ULTRASOUND-PLACED PAIN MANAGEMENT SYSTEM AND METHOD WITH SUBCUTANEOUS CATHETER

CROSS-REFERENCE TO RELATED APPLICATION

This application is a continuation-in-part of and claims priority in U.S. patent application Ser. No. 17/518,815, filed Nov. 4, 2021, which claims priority in U.S. Provisional Patent Application Ser. No. 63/200,204, filed Feb. 21, 2021, which are incorporated herein by reference in their entireties.

BACKGROUND OF THE INVENTION

1. Field of the Invention

The present invention relates generally to catheters, and in particular to a catheter system with an implantable port for administering anesthetics, e.g., nerve blocks, and other localized pharmacologic agents and treatments. A port placement method utilizes ultrasound imaging for placement in proximity to patients' nerves and nerve centers.

2. Description of the Related Art

Various medical procedures involve the administration of pharmacologic agents for achieving favorable outcomes. For example, anesthesiology typically involves anesthetizing patients during surgery and other medical and dental procedures. General anesthetics render patients unconscious for limited, predetermined periods of time, during which medical procedures, e.g., surgeries, are performed. Local anesthetics are commonly used for anesthetizing specific areas of patients, e.g., for dental procedures, surgeries performed on extremities, etc.

Well-established local anesthetic injection procedures include nerve blocks, peripheral nerve blocks, epidural blocks, subarachnoid blocks and spinal blocks. The purpose of these blocks is to inhibit transmission of pain or sensation, thus terminating the pain signals received by the nervous system. These blocks can be used to treat acute pain, as is used for surgical procedures, as well as chronic pain, and have been shown to decrease opioid use. Other suitable medicines and drugs used to modulate or control pain or extend the duration of the nerve block are often added to local anesthetics or used alone. New medicines currently in development that work at specific sodium channels show promise in providing superior pain control.

The field of palliative care involves treating patients who have been diagnosed with serious illnesses. Palliative care objectives include improving patient quality of life and minimizing disruption for caregivers, e.g., medical professionals and family members. Palliative care is a growing field in medicine. Population demographics in the United States, including an aging population, are likely to contribute to more palliative care cases and greater anticipated demand for adequate pain relief. End-of-life patients are often treated by hospice care medical service providers. Patients receiving hospice care often require medications for chronic pain.

Opioids represent a significant class of pain control drugs and are commonly prescribed for and administered to patients dealing with chronic pain, including hospice care patients. However, opioid-based pharmaceuticals have multiple disadvantages. Patient addiction and opioid dependency are significant concerns. Expense and stringent regulatory (e.g., FDA) control are additional factors. Moreover, patients can develop tolerances, which can necessitate switching treatment protocols and increasing required dosages to achieve effective outcomes. Non-opioid options for pain control are desirable and needed due to the deleterious side effects of chronic opioid use. Chronic pain, palliative, and hospice patients often have increased pain control requirements requiring escalating doses of opioids. As doses increase, so do the side effects, often leading to consequences that decrease quality of life or lead to death of the patient.

Catheters for administering medications, including anesthetics via patients' venous circulatory systems, are well-known in the art. For example, Luther U.S. Pat. No. 5,403,283 discloses a percutaneous port catheter assembly and method of use. Cai et al. U.S. Pat. No. 5,743,873 discloses methods for using catheter connectors and portals, and methods of assembly.

Local anesthetics are generally most effective when administered in proximity to patients' nerves. Relatively recent improvements in ultrasound technology enable healthcare providers to more precisely visualize and locate nerves and nerve centers, as compared to blind catheter placement techniques used previously. Ultrasound technology has sufficiently advanced so that precise placement of injections near nerves or nerve centers can be performed with real-time ultrasound imaging machines at patients' bedsides. Such ultrasound imaging machines are generally superior to other current visualization modalities due to their size, portability, quality imaging, visualization of deep anatomic structures and an absence of ionizing radiation. Ultrasound imaging machines of this kind are termed point-of-care-ultrasound systems (POCUS). POCUS can remove the necessity of transporting patients for treatment which can be painful, expensive and deleterious to their physical conditions.

Ultrasound relies on reflection of sound waves generated by an ultrasound probe. The sound waves are recaptured and analyzed to generate live, real-time images. Ultrasound waves are reflected according to the target anatomic structures' physical properties, including density, fluid characteristics (e.g., viscosity and flow mechanics). Differences in these properties allow generation of the ultrasound images. These properties, however, are often similar to each other and to the materials used to construct catheter systems. Because of this, it is often difficult to discern catheters from adjacent anatomy. This can lead to complications such as nerve damage from needle trauma, inadvertent vein or artery puncture, and injection of local anesthetic into the vascular system which can produce a syndrome termed Local Anesthetic Systemic Toxicity (LAST), which can produce cardiovascular collapse and death. Certain devices and anatomic structures are discernable with ultrasound and are thus called echogenic.

Long-term, local anesthetic delivery is desirable in treating disorders such as complex regional pain syndrome (CRPS), peripheral neuropathy and postherpetic neuralgia, among many others. The delivery of new medicines, such as sodium channel specific local anesthetics, will be well-suited for such a catheter system. Currently available systems, called percutaneous catheters, describe catheters that transverse the skin layer. Percutaneous catheters allow a limited time period for treatment of four to six days before the catheter must be removed. After this time period, the risk of infection caused by a catheter passing from outside the body to inside the body can supersede the benefits of pain relief. The nerve block catheter—port system of the present invention addresses infection risk by adding a port below the skin (subcutaneous) for injecting medicines. The port attaches to the nerve block catheter. The entire system lies below the epidermis.

A uniquely echogenic catheter that is suited for long-term use would be an improvement to the art and is desirable and needed.

A nerve block is an injection to decrease inflammation or "turn off" a pain signal along a specific distribution of nerve or group of nerves. This is achieved by injecting numbing medicines, i.e., local anesthetics, and other pain-inhibiting drugs. There are over 40 nerve blocks that are used in medicine today. As ultrasound gets more advanced and the visualization of anatomy becomes more clear, additional blocks will be possible.

The purpose of peripheral nerve blocks is to inhibit impulse transmission in a nerve or group of nerves, thus terminating the pain signal perceived by the nervous system. Nerve blocks can be used to treat acute pain (e.g., during surgery), as well as for treatment of chronic pain. Impulse blockade can be brief (hours) or prolonged (days), depending on the medication used in the block and the technique. If short-term pain control (e.g., hours) is required, medication can be administered via single injections. Longer-term pain control (e.g., days) can be provided via a percutaneous catheter.

Nerve blocks have been shown to decrease the use of opioids because the sensation of pain from the site of surgery is greatly diminished or is absent. Single injection nerve blocks generally last for 12-24 hours and percutaneous nerve blocks can last for three to four days. Nerve blocks have the potential to decrease opioid use beyond this short time window with our method to prolong the block greater than four to six days.

Currently, catheters that are placed near a nerve are brought out through the skin (percutaneous) and attached to a pump that delivers a local anesthetic for approximately three to four days. This is very effective pain control but has limitations. The catheter travels from the pump, through the skin, to terminates near the nerve. Any foreign body (a catheter in this case) that passes through the skin can be an avenue for bacteria to make its way into the below the skin and cause infection. Research shows that the chance of bacterial infection rises each day. Hence it is not recommended for current percutaneous nerve block catheters to remain in place for more than four days.

Port—catheter systems have been used for decades in patients where access is needed to the venous system, i.e., the catheter is placed in a vein. A port—catheter system where the catheter is in a vein is used for patients who are receiving chemotherapy, need frequent blood transfusions, etc. The nerve block catheter—port system of the present invention is the first-time a below-the-skin port has been described in combination with a nerve block catheter. Although the port is similar, the nerve block catheter is very different than a catheter meant to be placed in a vein. For example, such catheters can be made of different materials, can be designed to be visualized with ultrasound, have different mechanical properties (stiffness, diameter), and have a different structure. Catheter intended for used in a vein are generally not compatible with nerve block use.

Heretofore there has not been available a pain management system and method with the advantages and features of the present invention. These advantages and features include, without limitation: ultrasound visualization for anatomic imaging for placing catheters near nerves and nerve centers (bundles); producing ultrasound images that are uniquely different from anatomic structures to enable accurately placing catheter infusion ports, which are the most crucial system components, near patients' nerves and nerve centers. The aforementioned complications can thus be minimized or avoided.

SUMMARY OF THE INVENTION

In the practice of an aspect of the present invention, a pain management system is provided that includes an implantable port with an elastomeric septum, which is connected to a catheter. The catheter can be placed with its infusion ports in proximity to nerves or nerve centers using ultrasound imaging techniques and equipment and is designed to be uniquely visible (echogenic) when viewed with ultrasound. The catheter system is located in a patient's body below the skin layer (subcutaneous) to minimize infection risk. The port provides a conduit for injecting medicines and can be readily felt from above the skin by medical professionals allowing for placement of the Huber needle into the port. The catheter is fluidically connected to the port with infusion ports at the distal end. A programmable microprocessor can be connected to a medication control system for dispensing predetermined medication quantities continuously or intermittently. Alternatively, a syringe can be used for manually introducing medication via the implantable port.

A nerve block system that is placed below the skin allows medicines to be given long term. After the skin above the port is sterilized, it is accessed by a specially designed needle (e.g., a Huber needle). After the nerve block has been given via either a one-time dose or an infusion, the Huber needle can be removed. If a long-term infusion is needed, the access needle needs to be removed and the skin re-sterilized, e.g., at weekly intervals. The nerve block catheter—port system of the present invention can be used to provide long-term pain control for palliative, hospice and chronic pain patients.

A medication delivery method according to the present invention includes the steps of placing an implantable port, extending a catheter from the port to an affected area requiring treatment, and injecting medication administration as necessary to achieve a favorable outcome, such as healing or alleviating pain and discomfort. Medications can be delivered intermittently or continuously.

In another embodiment, a MEMS (microelectromechanical system) placed in the catheter can monitor nerves or nerve centers for abnormal function and provide ultrasonic, electrical or physical treatment according to a pre-programmed algorithm. For example, if a nerve injury causes insolated nerve dysfunction, the nerve may not activate in a normal physiological pattern. The MEMS sensor is activated by this electrical dysfunction and treatment is provided via a pMUT (Piezoelectric micromachined ultrasonic transducers), neuromodulatory actuator or other device according to predetermined programming on the microchip included in the MEMS.

In another embodiment, a MEMS can monitor nerve or nerve center and relay information related to function and/or dysfunction. This information can be transmitted by direct or wireless electrical connection to a suitable computing machine and used to monitor or guide treatment.

In another embodiment, the vibratory qualities of the catheter tip could provide treatment. Vibratory therapy is known to inhibit nociceptive receptors and treat pain in the setting of peripheral neuropathy among other disorders and could be provided to very specific nerve or nerve centers by the oscillatory method provided by electromagnetic or electrical energy, the activation of a MEMS and other herein described embodiments.

In one embodiment the port is accessed intermittently or continuously with a Huber, or other non-coring needle. If used continuously, this needle can be removed periodically, the skin sterilized, and a new sterile needle introduced to minimize infection risk.

In another embodiment, an echogenic marker that is discernable from anatomy is placed at the tip of the catheter near the infusion ports or in the wall of the catheter as an aid in placement of the catheter system. The echogenic marker can be comprised of biocompatible materials such as ceramics, polymethyl methacrylate (PMMA), titanium, stainless steel, or other suitable material. This echogenic structure can provide the medical professional with confirmation that the infusion ports of the catheter system are located in the desired location in relation to nerves or nerve centers.

In another embodiment, a wire coil is embedded in the catheter creating a solenoid and electrical conductors are extended to the distal end of the catheter. An echogenic magnet is placed in the solenoid and the system is energized via a time-varying current producing oscillatory movement of the magnet as a unique ultrasonic visual aid in placement of the catheter system. The system is energized by a nerve stimulator, as is commonly available in the medical setting, or a similar device suitable to produce the magnitude of electromagnetic field necessary to produce oscillatory movement. Nerve stimulators supply power in a regular on/off pattern per a predetermined frequency. As the solenoid in the catheter is energized, the echogenic magnet is induced to move due to electromagnetic energy. When the solenoid is de-energized, the magnet returns to its original position. This oscillatory movement can provide a unique visual identifier to the medical professional, thus confirming that the infusion ports of the catheter system are located in the desired location in relation to nerves or nerve centers.

Electrorheological (ER) and magnetorheological (MR) fluids are special classes of materials that can respond to the electrical field and magnetic field, respectively, resulting in a physical change from a liquid to a solid. In another embodiment, an amount of ER fluid is placed in the catheter system and electrical conductors are extended to the distal end of the catheter and energized by a nerve stimulator or similar suitable device for energizing the fluid to induce a physical change thereby making the catheter system more discernable when viewed with ultrasound. Likewise, a physical change in a MR fluid could be induced by creating a magnetic field by the use of a solenoid as described in the previous embodiment.

Piezoelectric micromachined ultrasonic transducers (pMUTs) have recently been developed which are devices that are small enough to be placed in close physical location or direct contact with nerves or nerve centers. pMUTs are a version of a microelectromechanical system (MEMS) that incorporate a piezoelectric crystal for the purpose of converting electrical energy to sound energy and vice versa. In another embodiment, these or similar devices are installed at the distal end the catheter in the catheter system, allowing direct mechanical stimulation of nerve or nerve centers, allowing precise ultrasonic treatment. pMUTS can be energized via the aforementioned embodiments for energizing the catheter system.

In another embodiment, a phase change agent is provided in the catheter tip to facilitate ultrasound detection.

In another embodiment, a stylet with a unique shape or device at its distal end could be placed in the catheter and used to induce movement of the distal end of the catheter to aid visualization with ultrasound.

BRIEF DESCRIPTION OF THE DRAWINGS

FIG. 3 is a fragmentary, cross-sectional view of an alternative embodiment catheter tip with an echogenic marker.

FIG. 4 is a fragmentary, cross-sectional view of another alternative embodiment catheter tip with a solenoid and magnet assembly.

FIG. 5 is a fragmentary, cross-sectional view of another alternative embodiment catheter tip with magnetorheological or electrorheological fluid.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Said terminology will include the words specifically mentioned, derivatives thereof and words of similar meaning. The definition of nerve designates peripheral nerves such as are commonly known, such as the saphenous, femoral, intercostal or radial nerves as well as numerous others. Nerve centers designate more proximal (e.g., closer to the central nervous system) nerve locations than peripheral nerves and include, but are not limited to, nerve roots, trunks, divisions, cords, and plexuses. Examples of these are the cervical roots, anterior division, lateral cord and the brachial plexus. Likewise, epidural or subarachnoid, as they are commonly referred to in the art, are an anatomic location that contains nerves, nerve roots and/or plexuses.

II. Ultrasound-Guided Catheter System 2

Figure 1:
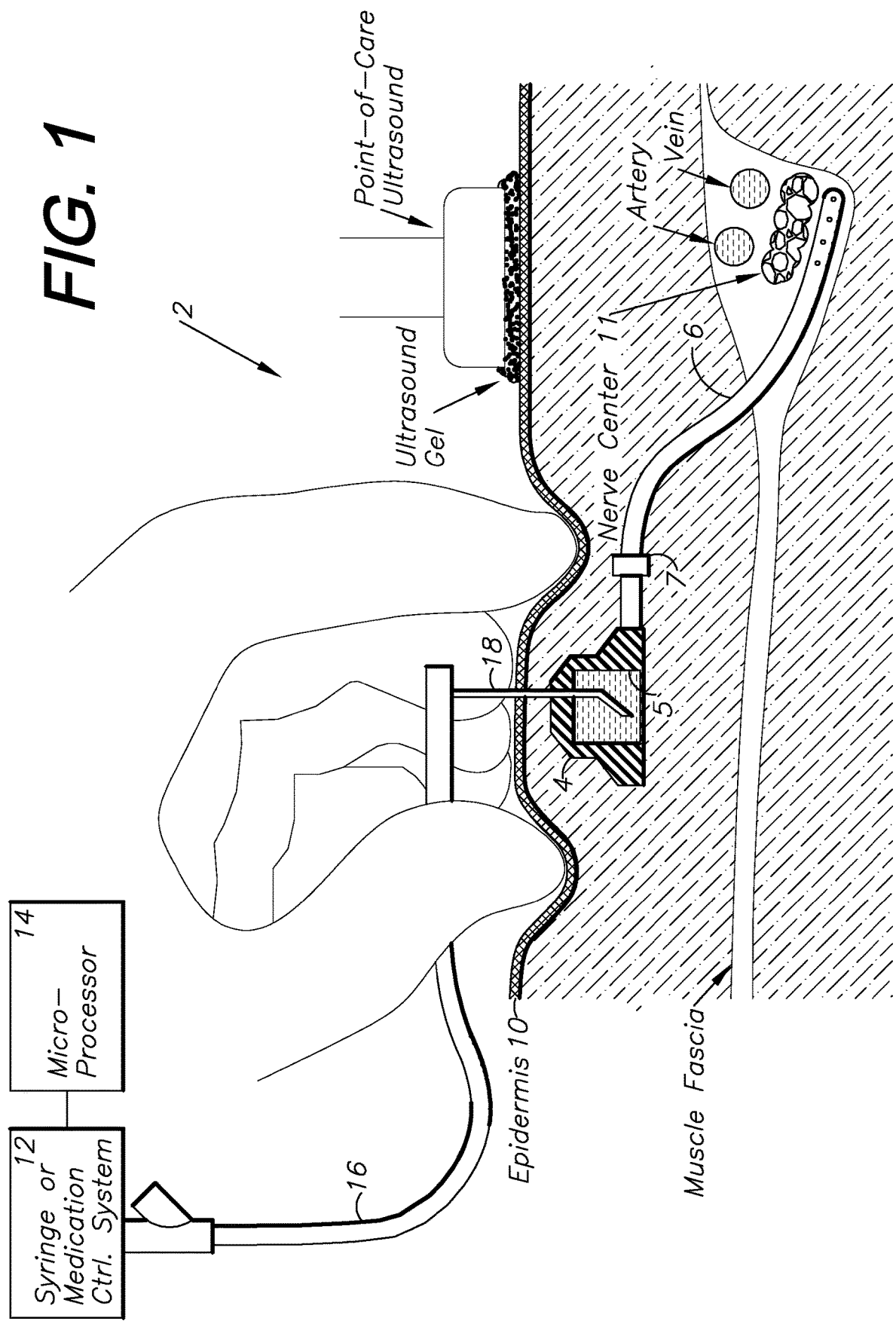
FIG. 1 a cross-sectional view of a catheter system embodying an aspect of the present invention, shown receiving a medication for transfusion in a patient.

A catheter system 2 embodying an aspect of the present invention is shown in FIG. 1 and generally includes an implantable port 4 connected to a catheter 6. The port 4 is preferably placed below the epidermis 10, and can be internally attached with sutures, surgical staples or some other attachment mechanism. The port 4 is preferably configured for receiving a quantity of a pharmacologic treatment, such as an anesthetic, a chemotherapy medication, etc. The port 4 can be constructed of ferrous or non-ferrous materials with a reservoir 5 and is designed for coupling with the catheter 6 via a coupler 7. The coupler 7 can be designed for repeated detachment from and attachment to the catheter 6 to facilitate replacement of the port 4 and catheter 6.

Additionally, it may be desired to temporarily detach the port 4 from the catheter 6 to inject pharmacologic agents into the catheter 6 to evaluate the placement of those medicines near nerves or nerve centers or evaluate function of the catheter 6. It may be desirable for the port 4 to be of smaller size in its height and diameter to allow for placement in a variety of anatomic locations to minimize discomfort and decrease the likelihood of skin ulceration due to pressure from outside the body to the skin over the port. The catheter 6 is fluidically connected to the port 4 and terminates in proximity to portions of the patient's nervous system to be anesthetized. Nerves and nerve centers 11 can be located using an ultrasound imaging procedure.

For placement of the catheter 6, a Tuohy needle, or some other suitable non-coring needle, is advanced under ultrasound guidance to a nerve or nerve center 11. The catheter is then advanced through the needle and the needle is withdrawn. In another embodiment, known as the Seldinger technique, a needle is advanced to the nerve or nerve center 11, a wire is advanced through the needle, the needle is withdrawn, and the catheter is exchanged over the wire.

In another embodiment commonly used for catheter placement, a breakaway sheath and wire system accomplishes the same purpose.

The catheter portion of the system is located so that the infusion ports are near nerve or nerve centers 11, but the port portion of the system is located in an anatomic location that is convenient for access of injection as well as comfort of the patient. A path below the skin from the catheter to the port can be created by tunneling, as is well known in the art for the placement of ventriculoperitoneal shunts or spinal cord stimulators, if the desired location for the port is some distance from the catheter.

As an example, it may be necessary, as in the case of epidural placement of the catheter in the midline of the back, for the port to be located on the patient's flank to prevent ulceration of the skin covering the port, for comfort of the patient and ease of injection. The catheter can be trimmed to length so the distance from the infusion ports of the catheter to the port can be specifically tailored for each patient, allowing the port to be placed in an anatomic location convenient for injection and with adequate fascia layers for securing the port with sutures or other method, with its septum facing outward.

A syringe or other medication control system 12 is connected to tubing 16 terminating at a needle 18. Huber and other suitable non-coring needles can be used for injecting medications into the subcutaneous port 4. The needle 18 can also comprise a stylet, which can be curved. Various medication dispensing devices can be used with the catheter system 2 of the present invention. For example, in lieu of a manually-operated syringe, a motorized pump can be provided. Moreover, operation of the medication control system 12 can be automated with a programmable microprocessor 14 for cycling the operation of a motorized pump to dispense medication at predetermined intervals consistent with a predetermined treatment protocol. Medicine control systems such as described are currently available and commonly used in medical settings. Moreover, various medications can be selectively administered, including, without limitation, anesthetics, chemotherapy medications, growth factors, antiseptics, etc.

The port 4 can be accessed intermittently or continuously with a Huber or other non-coring needle 18. If used continuously, this needle 18 can be removed periodically, the skin 10 sterilized, and a new sterile needle 18 introduced to minimize infection risk.

Figure 2:
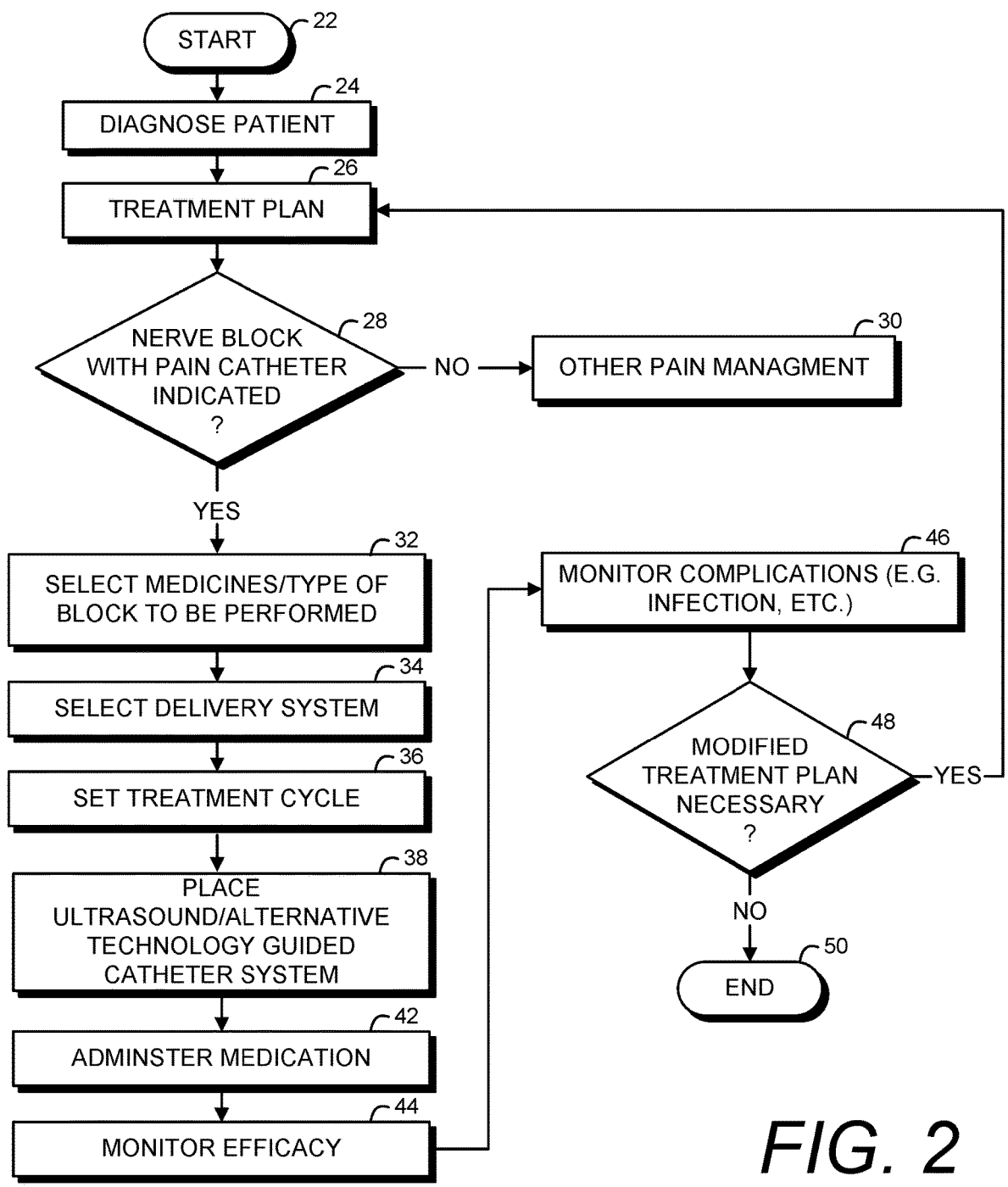
FIG. 2 is a flowchart showing a pain management treatment protocol method embodying an aspect of the present invention.

FIG. 2 is a flowchart showing an example of a medication administration method embodying an aspect of the present invention. From a start 22, the method includes the steps of diagnosing the patient at 24 and devising a treatment plan at 26. At decision box 28, a procedure including a nerve block with a pain catheter can be considered. If negative ("NO"), other pain management can be chosen at 30. If positive ("YES"), the protocol continues to selection of medicines and type of block to be performed at 32 and selection of a delivery mechanism at 34. The treatment cycle (e.g., intermittent, continuous, etc.) is set at 36. Step 38 involves placing an ultrasound/alternative technology guided catheter system.

Medication is administered at 42 and its efficacy is monitored at 44. Complications are monitored at 46 and can include, for example, infection, toxicity, etc. If a modified treatment plan is deemed necessary ("Yes" path from decision box 48), the protocol loops back to the treatment plan step 26. If "No," the treatment terminates at 50.

III. First Alternative Embodiment Catheter System 102 with Echogenic Marker 104

In another embodiment or aspect of the present invention, shown in FIG. 3, an echogenic marker 104 that is discernable from anatomy is placed at the tip of a catheter 106 near infusion ports 108 in the wall of the catheter 106 as an aid in placement of the catheter system 102. The echogenic marker 104 can be comprised of biocompatible materials such as ceramics, polymethyl methacrylate (PMMA), titanium, stainless steel, or other suitable material. This echogenic structure can provide the medical professional with confirmation that the infusion ports 108 of the catheter system 102 are located in the desired location in relation to nerves or nerve centers 11.

IV. Second Alternative Embodiment Catheter System 202 with Solenoid

In another alternative embodiment or aspect of the present invention, shown in FIG. 4, a wire coil solenoid 220 is embedded in a catheter 206. Electrical conductors 222 (−) and 224 (+) are extended to a distal end 226 of the catheter 206. An echogenic magnet 228 is placed in the solenoid 220 and the system 202 is energized via a time-varying current producing oscillatory movement of the magnet 228 as a unique ultrasonic visual aid in placement of the catheter system 202. The system is energized by a nerve stimulator, as is commonly available in the medical setting, or a similar device suitable to produce the magnitude of electromagnetic field necessary to produce oscillatory movement.

Nerve stimulators can supply power in a regular on/off pattern per a predetermined frequency. As the solenoid 220 in the catheter is energized, the echogenic magnet 228 is induced to move due to electromagnetic energy. When the solenoid is de-energized, the magnet returns to its original position. This oscillatory movement can provide a unique visual identifier to the medical professional, thus confirming that infusion ports 208 of the catheter system 202 are located in the desired location in relation to nerves or nerve centers 11.

V. Third Alternative Embodiment Catheter System 302 with Electrorheological (ER) and Magnetorheological (MR) Fluids In a third alternative embodiment or aspect of the invention shown in FIG. 5, a catheter system 302 includes a quantity of ER or MR fluid 320 placed in a reservoir 321 in the catheter distal end 326. The catheter system 302 includes infusion ports 308. Negative and positive electrical conductors 322, 324 are extended to the catheter distal end 326 and energized by a nerve stimulator or similar suitable device for energizing the fluid 320 to induce a physical change, thereby making the catheter 306 more discernable when viewed with ultrasound. Likewise, a physical change in a MR fluid could be induced by creating a magnetic field by the use of a solenoid as described in the previous embodiment 202.

Figures 6, 7:
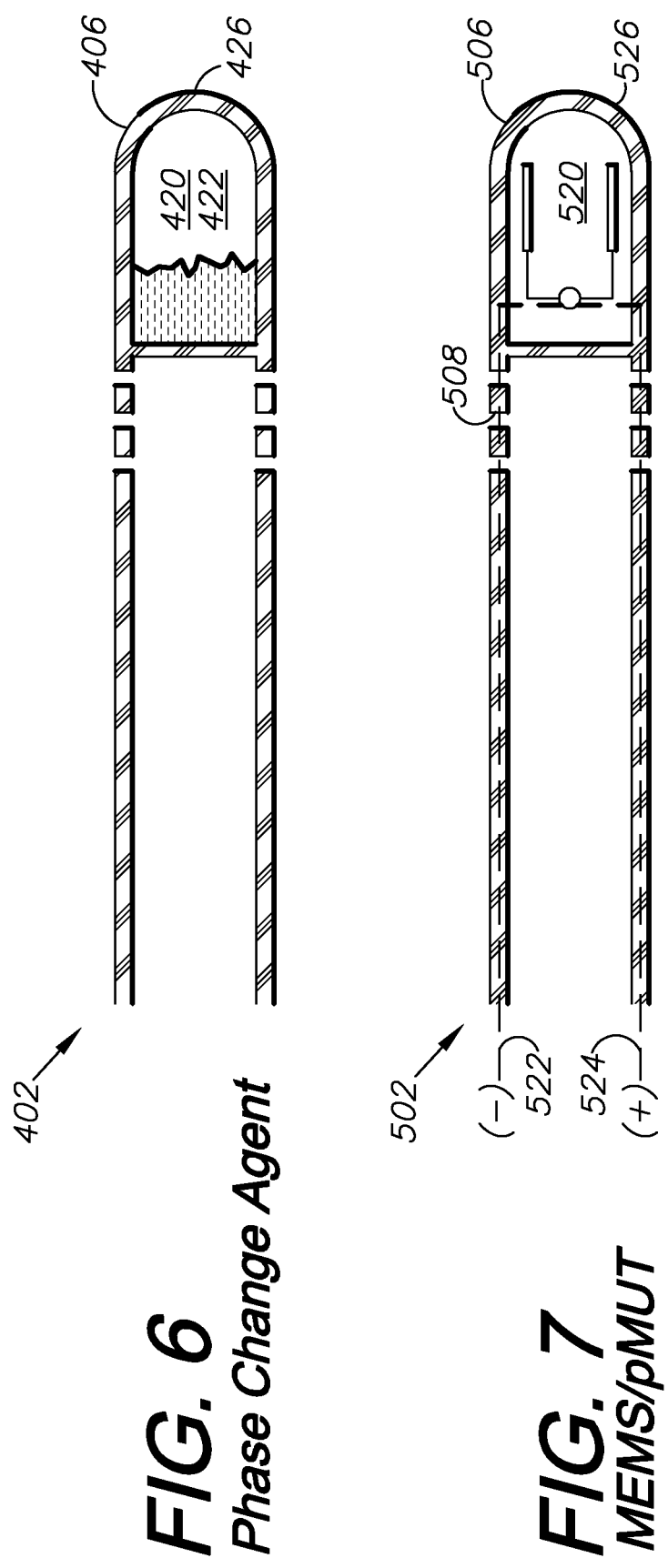
FIG. 6 is a fragmentary, cross-sectional view of another alternative embodiment catheter tip with a phase change agent.
FIG. 7 is a fragmentary, cross-sectional view of another alternative embodiment, catheter tip with a micro-electronic mechanical system or a piezo-electronic micro-machined ultrasonic transducer.

VI. Fourth Alternative Embodiment Catheter System 402 with Phase Change Agent FIG. 6 shows a catheter system 402 comprising another alternative embodiment or aspect of the present invention with a phase change agent 420 contained within a reservoir 422 in a distal end 426 of a catheter 406 with infusion ports 408. Phase change agents, such as, but not limited to perflourocarbons, have a boiling point near body temperature so that vaporization can be induced by the acoustic energy provided by the ultrasound probe producing expansion in volume. This volume change is visible via ultrasound. In another embodiment, phase change agents are encapsulated in the catheter system and induced by energy of the ultrasound probe to create a unique visual marker. When the ultrasound probe is removed, the phase change agent returns to the prior state.

VII. Fifth Alternative Embodiment Catheter System 502 with MEMS or pMUT

FIG. 7 shows a catheter system 502 embodying a fifth alternative embodiment or aspect of the present invention with a microelectromechanical system (MEMS) or a piezoelectric micro-machined ultrasonic transducer (pMUT) component 520. The component 520 is located in a closed, distal end 526 of a catheter 506 with infusion ports 508. Electrical conductors 522 (−) and 524 (+) are connected to a nerve stimulator, which can sequentially energize and deenergize the component 520 to achieve a desired result by varying the amplitude and frequency of the energizing signals.

The Microlectromechanical System (MEMS) catheter system 502 can be fabricated using semiconductor materials and incorporating mechanical components, sensors, actuators, and electronic elements with feature sizes ranging from a few millimeters to microns gauge. In another embodiment, MEMS can be incorporated in the catheter system and energized to induce a movement of a portion of the catheter system via an actuator that would be uniquely visible via ultrasound.

A distinct advantage of the herein described catheter system 502 is that the location of the port is immediately below the skin layer, minimizing distance to the external energy source, with the result of maximizing transfer efficiencies. The underside of the port, opposite of the septum, is geometrically suitable for placement of a receiving coil to be in parallel with a transmitting coil placed outside the skin. The coil that is embedded on the port can be connected to a conducting lead which is embedded in the catheter and terminating at the distal of end of the catheter in proximity to nerves or nerve centers and designed to conduct neuromodulation signals.

In another embodiment, ultrasonic energy transfer can be utilized to transcutaneously energy the catheter system. This utilizes the known piezoelectric effect that utilizes the conversion of ultrasonic energy to electrical energy. Ultrasonic transfer of energy allows longer power transmission distances and is free of electromagnetic interference. In this scheme, a piezoelectric transducer that is external to the skin layer faces a piezoelectric receiver embedded in the port and under the skin layer allowing transmission ultrasonic energy in either direction without penetrating the skin layer. Energy is transmitted through the skin layer via ultrasonic energy from the transducer to the receiver and is converted to electricity. Electrical energy can then be utilized to energize the other herein described embodiments.

VIII. Ultrasound-Placed Pain Management Methods with Subcutaneous Catheters

The ultrasound-placed pain management systems with subcutaneous catheters can be utilized for a variety of treatment protocols. Moreover, they are adaptable for a variety of medications. Automated systems, e.g., with programmable microprocessors, can be programmed for providing consistent, regular treatments as indicated. Moreover, patients' healing progress can be closely monitored and treatment protocols adjusted or terminated for achieving optimal patient outcomes.

IX. Conclusion

The catheter systems and methods of the present invention can be adapted to accommodate a variety of medical conditions and treatment protocols. For example, antiseptics for infection control and growth factors for promoting reepithelialization can be introduced to a wound site.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A catheter system for administering medication to a patient, which system includes:
   a medication dispenser configured for placement externally to the patient;
   a medication port configured for placement subcutaneously to the patient;
   a needle configured for injecting the medication into said medication port;
   tubing configured for connecting said medication dispenser and said needle;
   a catheter configured for fluidically connecting to said medication port and terminating at a distal end internally within the patient, said catheter including an infusion port configured for discharging the medication internally within the patient;
   a medication control system connected to said medication dispenser and configured for selectively injecting the medication to said catheter;
   said medication control system configured for injecting the medication in predetermined dosages to said port;
   said medication control system configured for injecting the medication at predetermined time intervals;
   a point-of-care ultrasound imaging system configured for placing said catheter;
   said point-of-care ultrasound imaging system configured for imaging the patient's neurology;
   said point-of-care ultrasound imaging system configured for imaging said catheter and patient nerve centers in real time;
   said point-of-care ultrasound imaging system configured for use in guiding said catheter for medication discharge in proximity to a patient nerve center;

said catheter system configured for administering nerve block medications and other medications for treating nerve-related diseases;

said catheter including an echogenic marker located in said catheter distal end;

said echogenic marker comprising a microelectro-mechanical system encapsulated in said catheter distal end;

said microelectro-mechanical system including a Piezoelectric micro-machined ultrasonic transducer (pMUT) encapsulated in said catheter distal end;

a nerve stimulator connected to said pMUT and configured for energizing said pMUT with varying amplitude and frequency energizing signals; and said pMUT configured for detection by said point-of-care ultrasound imaging system for optimizing placement of said catheter distal end relative to the neurological system of the patient and thereby optimizing the effectiveness of the injected medication.

\* \* \* \* \*